US009387219B2

(12) United States Patent
Berry et al.

(10) Patent No.: US 9,387,219 B2
(45) Date of Patent: Jul. 12, 2016

(54) EDIBLE COMPOSITION

(75) Inventors: Mark John Berry, Sharnbrook (GB);
Mark Ian Fowler, Sharnbrook (GB);
Alan David Heath, Sharnbrook (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/122,355

(22) PCT Filed: May 29, 2012

(86) PCT No.: PCT/EP2012/059956
§ 371 (c)(1),
(2), (4) Date: Nov. 26, 2013

(87) PCT Pub. No.: WO2012/168108
PCT Pub. Date: Dec. 13, 2012

(65) Prior Publication Data
US 2014/0107052 A1    Apr. 17, 2014

(30) Foreign Application Priority Data

Jun. 6, 2011    (EP) .................................... 11168797

(51) Int. Cl.
*A61K 31/7034* (2006.01)
*A61K 31/7048* (2006.01)
*A23L 1/30* (2006.01)
*A61K 31/352* (2006.01)
*A61K 31/715* (2006.01)

(52) U.S. Cl.
CPC ........... *A61K 31/7048* (2013.01); *A23L 1/3002* (2013.01); *A61K 31/352* (2013.01); *A61K 31/7034* (2013.01); *A61K 31/715* (2013.01); *A23V 2002/00* (2013.01)

(58) Field of Classification Search
None
See application file for complete search history.

(56) References Cited

U.S. PATENT DOCUMENTS

| 8,198,319 B2 | 6/2012 | Ahrens et al. |
| 2004/0131749 A1 | 7/2004 | Grabiel et al. |
| 2005/0048149 A1 | 3/2005 | Gaudout et al. |
| 2006/0189512 A1 | 8/2006 | Ehrenkranz |
| 2007/0009615 A1 | 1/2007 | Zhong |
| 2007/0036874 A1 | 2/2007 | Zhong |
| 2008/0096825 A1 | 4/2008 | Ehrenkranz |
| 2010/0166851 A1 | 7/2010 | Dallas |
| 2010/0227828 A1 | 9/2010 | Gokaraju et al. |
| 2010/0247686 A1 | 9/2010 | Zhong |

FOREIGN PATENT DOCUMENTS

| CN | 101674821 A | 3/2010 |
| CN | 101991593 A | 3/2011 |
| EP | 0330240 A1 | 8/1989 |
| EP | 0330240 B1 | 1/2003 |
| EP | 1576893 A1 | 9/2005 |
| FR | 2935096 A1 | 2/2010 |
| JP | 2002080362 | 3/2002 |
| JP | 2004182685 | 7/2004 |
| JP | 2004229615 | 8/2004 |
| JP | 2011140457 | 7/2011 |
| KR | 20090125918 A | 12/2009 |
| WO | WO0025795 A1 | 5/2000 |
| WO | WO02076241 A1 | 10/2002 |
| WO | WO0234073 | 5/2005 |
| WO | WO2005070441 A1 | 8/2005 |
| WO | WO2006031293 A2 | 3/2006 |
| WO | WO2006074278 A2 | 7/2006 |
| WO | WO2006083666 A1 | 8/2006 |
| WO | WO2006097660 A1 | 9/2006 |
| WO | WO2007026101 A1 | 3/2007 |
| WO | WO2008011363 A2 | 1/2008 |
| WO | WO2008135643 A1 | 11/2008 |
| WO | WO2010066852 A1 | 6/2010 |

OTHER PUBLICATIONS

Maritim et al. J Biochem Molecular Toxicology, vol. 17, No. 1, 2003.*
Wright et al. Int J Clin Pract, Mar. 2006, 60, pp. 308-314.*
Baldea, Inhibition of intestinal gluocose absorption by anti-diabetic medicinal plants derived from the James Bay Cree tradional pharmacopeia, Journal of Ethnopharmacology, 2010, 473-482, 132, CA.
Boyer, Uptake of Quercetin and Quercetin 3-Glucoside from whole onion and apple peel extracts by Caco-2 cell monolayers, Journal of Agricultural and Food Chemistry, Oct. 16, 2004, 7172-7179, 52, US.
Dupont, Polyphenols from alcoholic apple cider are absorbed, metabolized and excreted by humans, The Journal of Nutrition, 2001, 172-175, ., GB.

(Continued)

*Primary Examiner* — Layla Berry
(74) *Attorney, Agent, or Firm* — Greenberg Traurig, LLP

(57) ABSTRACT

Foods or meals high in available carbohydrate such as sucrose or starch increase post-prandial blood glucose concentrations. Repeated high post-prandial plasma glucose "spikes" are associated with an increased risk of developing type II diabetes. Unregulated glycemic excursions are undesirable, and any reduction or "blunting" of the post-prandial glucose concentration in blood is potentially beneficial. This invention relates to an edible composition for delay of intestinal glucose uptake through synergistic inhibition of both active sodium glucose co-transporter 1 (SGLT1) and passive glucose transporter 2 (GLUT2) leading to flattening or blunting of the post-prandial glucose peak. Thus in a first aspect of the invention, an edible composition is provided, the composition comprising at least 5% dry weight at least one flavonoid aglycone and at least 5% dry weight at least one flavonoid glucoside, wherein the flavonoid glucoside is at least 20%, preferably at least 40%, most preferably at least 60% more resistant to hydrolysis by lactase phloridzin hydrolase than quercetin-4-glucoside, and wherein the flavonoid aglycone is a GLUT 2 inhibitor and the flavonoid glucoside is a SGLT 1 inhibitor.

7 Claims, 5 Drawing Sheets

(56) References Cited

OTHER PUBLICATIONS

Gao, Highly variable contents of phenolics in St. John's Wort products affect their transport in the human intestinal Caco-2 cell model: Pharmaceutical and Biopharmaceutical rationale for product standardization, Journal of Agricultural and Food Chemistry, May 7, 2010, 6650-6659, 58, US.

Johnston, Possible role for apple juice phenolic compounds in the actue modification of flucose tolerance and gastrointestinal hormone secretion in humans, Journal of the Science of Food and Agriculture, 2002, 1800-1805, 82, GB.

Manzano, Polyphenols and phenolic acids from strawberry and apple decrease glucose uptake and transport by human intestinal Caco-2 cells, Molecular Nutrition of Food Research, 2010, 1-8, 54, GB.

Nemeth, Deglycosylation by small intestinal epithelial cell B-glucosidases is a critical step in the absorption and metabolism of dietary flavonoid glycosides in humans, European Journal of Nutrition, 2003, 29-42, 42, GB.

Scow, Absence of Evidence of Translocation of GLUT2 to the Apical Membrane of Enterocytes in Everted Intestinal Sleeves, Journal of Surgical Research, 2010, 1-6, ., US.

Eid et al, Stimulation of AMP-activated protein kinase and enhancement of basal gluose uptake in muscle cells by quercetin and quercetin glycosides, active principles of the antidiabetic medicinal plant Vaccinium vitis-idaea, Molecular Nutrition and Food Research, 2010, 991-1003. 54, CA.

Jackson et al, Effects of processing on the content and composition of isoflavones during manufacturing of soy beverage and tofu, Process Biochemistry, 2002, 1117-1123, 37, CA.

EP Search Report EP 11 16 8797 dated Sep. 22, 2011.

PCT Int'l Search Report PCT/EP2012/059956 dated Sep. 14, 2012.

Node et al., Postprandial hyperglycemia as an etiological factor in vascular failure, Cardiovascular Diabetology, (2009), 8:23, p. 1-10.

* cited by examiner

EDIBLE COMPOSITION

Foods or meals high in available carbohydrate such as sucrose or starch increase post-prandial blood glucose concentrations. According to Node et al. (Cardiovascular diabetology, 8, 23 (2009)), repeated high post-prandial plasma glucose "spikes" are associated with an increased risk of developing type II diabetes. Unregulated glycemic excursions are undesirable, and any reduction or "blunting" of the post-prandial glucose concentration in blood is potentially beneficial. This invention relates to an edible composition for delay of intestinal glucose uptake through synergistic inhibition of both active sodium glucose co-transporter 1 (SGLT1) and passive glucose transporter 2 (GLUT2) leading to flattening or blunting of the post-prandial glucose peak.

SUMMARY OF THE INVENTION

In a first aspect of the invention, an edible composition is provided, the composition comprising at least 5% dry weight at least one flavonoid aglycone and at least 5% dry weight at least one flavonoid monoglucoside, wherein the flavonoid monoglucoside is at least 20%, preferably at least 40%, most preferably at least 60% more resistant to hydrolysis by lactase phloridzin hydrolase than quercetin-4-glucoside, and wherein the flavonoid aglycone is a GLUT 2 inhibitor and the flavonoid monoglucoside is a SGLT 1 inhibitor.

Lactase phloridzin hydrolyase (LPH), a beta-galactosidase, is an enzyme found in the small intestine involved in the hydrolysis of the disaccharide lactose into its constituent galactose and glucose monomers. In particular, the enzyme hydrolyses the beta-glycosidic bond in D-lactose. Deficiency of this enzyme causes lactose intolerance. LPH also has glucosidase activity. Thus it is essential that the flavonoid glucoside exhibits a degree of resistance to hydrolysis by LPH in the small intestine where glucose absorption, via the glucose transporters, takes place.

By the term "at least 20% more resistant to hydrolysis by LPH than quercetin-4-glucoside" is meant that the rate of hydrolysis by LPH is at least 20% lower than that for quercetin-4'-glucoside. Thus the rate would be zero if 100% more resistant to hydrolysis by LPH than quercetin-4-glucoside.

By the term "flavonoid aglycone" is meant an unglycosylated flavonoid. By the term "flavonoid monoglucoside" is meant a flavonoid attached to a single glucose unit. By the term "GLUT 2 inhibitor" is meant a compound which inhibits the transmembrane carrier protein known as passive glucose transporter 2. By the term "SGLT1 inhibitor" is meant a compound which inhibits the transmembrane carrier protein known as sodium glucose co-transporter 1.

The flavonoid aglycone may be selected from the group consisting of flavone aglycones, flavanol aglycones, flavanone aglycones, isoflavone aglycones and mixtures thereof. Thus by the terms "flavone aglycone", "flavanol aglycone", "flavanone aglycone" and "isoflavone aglycones" are meant an unglycosylated flavone, flavanol, flavanone and isoflavone respectively. In particular, the flavonoid aglycone may be selected from the group consisting of apigenin, luteolin, quercetin, kaempferol, myricetin, naringenin, pinocembrin, hesperetin, genistein and mixtures thereof.

The flavonoid monoglucoside may be selected from the group consisting of luteolin-7-glucoside, apigenin-8-C-glucoside, kaempferol-7-O-glucoside, kaempferol-3-O-glucoside, naringenoin-7-O-glucoside, daidzein-8-glucoside, cyanidin-3-glucoside, quercetin-3-glucoside, pelagonidin-3-glucoside, malvidin-3-glucoside, delphinidin-3-glucoside and mixtures thereof.

The molar ratio of flavonoid aglycone to flavonoid monoglucoside may be in the range 4:1 to 1:4, preferably 3:1 to 1:3, most preferably 2:1 to 1:2.

The composition may comprise no more than 50%, preferably no more than 10%, most preferably no more than 2% by weight flavonoid aglycone, and separately no more than 50%, preferably no more than 10%, most preferably no more than 2% by weight flavonoid monoglucoside. Thus at a level of no more than 2% by weight flavonoid aglycone, the composition must comprise water in order for the composition to comprise at least 5% dry weight at least one flavonoid aglycone.

The composition is preferably in the form of a daily dose, the daily dose comprising at least 50 micromoles, preferably at least 100 micromoles, most preferably at least 250 micromoles of flavonoid aglycone and at least 50 micromoles, preferably at least 100 micromoles, most preferably at least 250 micromoles of flavonoid monoglucoside.

The inventive composition may be in the form of a packaged beverage comprising no more than 99.95% w/w water. It may also be in the form of a dry powder contained in a sachet, the dry powder suitable for addition to a meal.

In a second aspect of the invention, a method of reducing post-prandial blood glucose peak amplitude or glycemic response in a non-diabetic person is provided, the method comprising the steps of:
(a) oral administration of the composition of the first aspect of the invention to the non-diabetic person; and
(b) oral administration of saccharide to the non-diabetic person;
wherein step (a) is simultaneous with, precedes by 0 to 90, preferably 0 to 60 minutes, or follows by 0 to 30 minutes step (b), and wherein the saccharide comprises or is glucose.

In a third aspect of the invention, a method for treating a person in need thereof for type 2 diabetes is provided, the method comprising the steps of:
(a) oral administration of the composition of the first aspect of the invention to the person in need thereof; and
(b) oral administration of saccharide to the person in need thereof;
wherein step (a) is simultaneous with, precedes by 0 to 90, preferably 0 to 60 minutes, or follows by 0 to 30 minutes step (b), and wherein the saccharide comprises or is glucose.

The saccharide may be selected from the group consisting of polysaccharide, oligosaccharide, disaccharide, monosaccharide and mixtures thereof.

In a fourth aspect of the invention, a composition according to the first aspect of the invention is provided for use in reducing post-prandial blood glucose peak amplitude or glycemic response in a non-diabetic person In a fifth aspect of the invention, a composition according to the first aspect of the invention is provided for use in the treatment of type 2 diabetes.

In a sixth aspect of the invention, use of a composition according to the first aspect of the invention is provided for the manufacture of a medicament for reducing post-prandial blood glucose peak amplitude or glycemic response in a non-diabetic person.

In a seventh aspect of the invention, use of a composition according to the first aspect of the invention is provided for the manufacture of a medicament for treatment of type 2 diabetes.

BRIEF DESCRIPTION OF THE FIGURES

The invention is illustrated with reference to the figures which show in.

DETAILED DESCRIPTION OF THE INVENTION

Example 1

Identification of SGLT1 and GLUT2 Inhibitors

Routine Cell Culture

Figure 1:
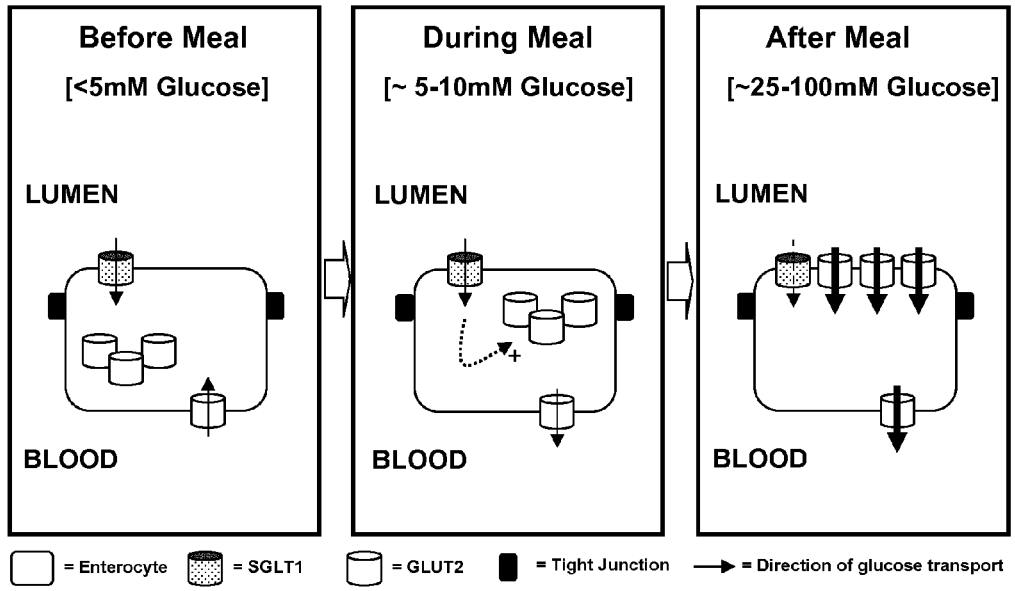
FIG. 1 a model of the glucose concentration timeline during a meal.

Human epithelial colorectal adenocarcinoma (Caco-2) cells were obtained from the American Type Culture Collection (ATCC) and cultured in Growth Medium consisting of Dulbecco's modified Eagle's medium (containing Glutamax-1, 4.5 g/L D-glucose and 25 mM 4-(2-hydroxyethyl)-1-piperazine ethanesulphonic acid (Hepes) (Invitrogen)), 10% foetal bovine serum (Sigma), 1% non-essential amino acids (Invitrogen) and 1 mM sodium pyruvate (Sigma)). The cells were routinely passaged at approximately 80% confluence using TrypLE™ Express Stable Trypsin-Like Enzyme (Invitrogen) to detach the cells, and seeded at approximately 114 cells per $mm^2$ in fresh tissue culture flasks. Only cells between the passage numbers 45 and 49 were used for experiments.

Preparation of Differentiated Caco-2 Cell Monolayers

Corning® HTS Transwell® 96 well permeable insert supports (Sigma) were collagen coated with 40 μl of 50 μg/ml rat tail collagen type I (BD Biosciences) in 0.02 M acetic acid for one hour at room temperature under sterile conditions. The inserts were washed twice in phosphate buffered saline (PBS (Invitrogen)) and the Caco-2 cells seeded into the inserts at $9.6 \times 10^5$ cell/ml (75 μl per insert) in Growth Medium and 30 ml of Growth Medium added to the feeder plate below. The cells were left to attach to the collagen matrix and form monolayers over 48 hours at 37° C., 5% $CO_2$. Both inserts and feeder plate were washed in PBS and the cells incubated with BD Entero-STIM™ Enterocyte Differentiation Medium containing MITO+™ Serum Extender solution (both BD Biosciences), 75 μl per insert and 30 ml in the feeder plate, for a further 48 hours at 37° C., 5% $CO_2$.

Glucose Transport Inhibitor Cell Screening Assay

Differentiated cell monolayers were washed gently in Dulbecco's Phosphate Buffered Saline containing $CaCl_2$ and $MgCl_2$ (PBS(+) (Invitrogen)) and the inserts transferred to a new Corning® HTS Transwell®-96 well receiver plate (Sigma). The cells were incubated with fresh PBS(+) (75 μl per insert and 225 μl per well) for 60 minutes at 37° C., 5% $CO_2$. The PBS(+) was gently aspirated and replaced with 75 μl per insert of either 5 mM D-glucose (Sigma)±test active or 25 mM D-glucose±test active in triplicate and 225 μl per well of PBS(+) quickly added to each well. The 5 mM glucose wells and the 25 mM glucose wells were incubated at 37° C., 5% $CO_2$ for 15 minutes and 30 minutes, respectively. Details of all the actives tested are found in table 1. The cell inserts were transferred to a new receiver plate, the supernatant gently aspirated from the cells and replaced with 100 μl of 100 μM of Lucifer Yellow (Sigma) solution to confirm the integrity of the monolayers. 225 μl of PBS(+) was added to each well and incubated at 37° C., 5% CO2 for 1 hour. The cell inserts were then discarded and the permeability of the membranes to Lucifer Yellow checked by measuring the fluorescence of the samples at 485 nm (excitation) and 530 nm (emission) on a Spectramax Gemini EM fluorescence microplate reader.

Glucose Assay

The amount of glucose transported across the cell monolayers was measured using a glucose assay based on Invitrogen's Amplex Red Glucose/Glucose oxidase Assay Kit. Briefly, 50 μl of each test sample was transferred to a black sided/clear bottom 96-well plate (Greiner Bio-One) to which 100 µl of reaction buffer (0.5 µl 10 mM Ampliflu Red, 1 µl 10 U/ml Horse Radish peroxidase, 1 µl 100 U/ml glucose oxidase and 97.5 µl PBS (all Sigma)) was added. After 10 minutes incubation at room temperature, the fluorescence of the samples were measured at 530 nm (excitation) and 590 nm (emission) on a Spectramax Gemini EM fluorescence microplate reader and the glucose concentration extrapolated from a standard curve.

Table 1 shows the percentage of inhibition of each test active against the transport of glucose across a differentiated Caco-2 cell monolayer. At the lower D-glucose concentration of 5 mM, the early transport of glucose across the cell monolayer is predominantly through the apically expressed, high affinity, low capacity SGLT1 glucose transporter. At higher D-glucose concentrations, the SGLT1 transporter becomes saturated and consequently the majority of glucose transport across the monolayer is driven by the low affinity, high capacity GLUT2 transporter that is targeted to the apical membrane only following an initial SGLT1-dependent transport of glucose. The screening cell model, detailed in the methods above, is designed to take advantage of these differences in the optimal conditions for each transporter to identify both SGLT1 and GLUT2 specific inhibitors. While both SGLT1 and GLUT2 on the apical membrane transport glucose into the enterocyte, GLUT2 is also expressed in the basolateral membrane where it is essential for the transport of glucose out of the cell. Hence, GLUT2 specific inhibitors will not only block the apically targeted transporters at high D-glucose concentrations (25 mM), they will also enter the cell and block the exit of glucose from the enterocyte at low D-glucose concentrations (5 mM). Therefore, to differentiate between inhibition of apical and basolateral transporters, each active was tested at both 5 mM D-glucose for 15 minutes and 25 mM D-glucose for 30 minutes. Actives were classed as SGLT1 inhibitors if they exhibited at least 20% inhibition of glucose transport at 5 mM D-glucose and a corresponding no more than 20% inhibition at 25 mM D-glucose. Actives that were able to inhibit glucose transport by at least 20% in both conditions were classed as GLUT2 specific inhibitors. This approach was qualified through the use of the widely recognised specific inhibitors of both SGLT1 and GLUT2, namely phloridzin and phloretin respectively.

The foregoing glucose transport cell model was described by Kellett et al. (Diabetes, 54, 10, 3056-62 (2005)) and illustrated by FIG. 1 designed to mimic the localised changes in glucose concentration in the small intestine during the consumption of a carbohydrate rich meal. Before the meal, the concentration of free glucose in the lumen of the intestine is low (<5 mM) and the apically expressed SGLT1 transporter actively transports any available glucose into the enterocyte. GLUT2 transporters are also active on the basolateral membrane of the enterocyte, transporting glucose from the blood into the cell to maintain cellular metabolism if required. During a meal, the local concentration of glucose begins to increase (5-10 mM) and is transported from the intestinal lumen by SGLT1 and subsequently into the systemic circulation via GLUT2. As a consequence of this initial glucose transport across the enterocyte, intracellular stores of GLUT2 are mobilised and targeted to the apical membrane. Shortly after the meal, very high local concentrations of glucose occur (25-100 mM) as the carbohydrate content of the meal is broken down into monosaccharides by alpha-glucosidase enzymes located on the apical enterocyte membrane. At these high levels of glucose, the high affinity, low capacity transporter SGLT1 becomes saturated and the majority of glucose transport across the enterocyte is due to the low affinity, high capacity GLUT2 transporters now present in the apical membrane.

Table 1 demonstrates that for inhibition of SGLT1, a flavonoid monoglucoside is required as confirmed by luteolin-7-glucoside, apigenin-7-glucoside, apigenin-8-c-glucoside, kaempferol-3-glucoside, kaempferol-7-glucoside, quercetin-3-glucoside, quercetin-4-glucoside, naringenin-7-glucoside, eriodictiol-7-glucoside, daidzein-8-c-glucoside, daidzein-7-glucoside, cyanidin-3-glucoside, malvidin-3-o-glucoside, delphinidin-3-glucoside and pelargonidin-3-glucoside. Indeed, the presence of an additional glucose moiety on the chemical structure destroys this inhibitory action as demonstrated by quercetin-3,4'-diglucoside. The specificity for a glucoside is confirmed by the absence of SGLT1 inhibitory activity by other flavonoid glycosides tested, including cyanidin-3-rutinoside and malvidin-3-O-galactoside. In addition, the lack of SGLT1 inhibitory activity shown by the hydroquinone monoglucoside, arbutin, reinforces the importance of a flavonoid structure in the glucoside molecule. Other non-flavonoid glucosides alleged by Welsch et al. (J. of Nutrition, 119, 11, 1698-704 (1989)) to be glucose transporter inhibitors such as chlorogenic acid, caffeic acid and rosmarinic acid (an ester of caffeic acid) showed no inhibitory activity in this cell model for either SGLT1 or GLUT2 inhibition. Table 1 also shows that all the aglycones tested from each flavonoid class selected, except the anthocyanidins, were confirmed as GLUT2 inhibitors.

Example 2

Synergy Between SGLT1 and GLUT2 Inhibitors

Preparation of Differentiated Caco-2 Cell Monolayers

Caco-2 cells were cultured and routinely passaged as described in example 1. Caco-2 cells were seeded into Bio-Coat HTS Fibrillar Collagen Multiwell Inserts (BD Biosciences) at $2.5 \times 10^5$ cell/ml (500 µl per insert) in Growth Medium and 30 ml of Growth Medium added to the feeder plate below. The cells were left to attach to the collagen matrix and form monolayers over 24 hours at 37° C., 5% $CO_2$. Both inserts and feeder plate were washed in PBS and the cells incubated with BD Entero-STIM™ Enterocyte Differentiation Medium containing MITO+™ Serum Extender solution (both BD Biosciences), 500 µl per insert and 30 ml in feeder plate, for a further 48 hours at 37° C., 5% $CO_2$.

TABLE 1

Actives tested for SGLT1 and GLUT2 inhibition activity in Caco-2 cells using 5 mM D-glucose for 15 minutes and 25 mM D-glucose for 30 minutes, respectively. The assigned class of transporter inhibited by each active is based on SGLT1 inhibitors having ≥20% inhibition of glucose transport at 5 mM D-glucose and ≤20% inhibition at 25 mM D-glucose, and GLUT2 inhibitors having ≥20% inhibition at both 5 mM and 25 mM D-glucose levels.

| Chemical Family: | | Test Active[a] | Solvent | % Glucose Transport inhibition | | Class[b] | Supplier |
|---|---|---|---|---|---|---|---|
| | | | | 5 mM | 25 mM | | |
| Chalcone | | Phloridzin | EtOH | 57.57 | 18.42 | SGLT1 | Sigma |
| | | Phloretin | EtOH | 86.77 | 76.14 | GLUT2 | Sigma |
| Flavonoids: | Flavones | Apigenin | DMSO | 56.83 | 49.28 | GLUT2 | Sigma |
| | | Luteolin | DMSO | 77.42 | 63.24 | GLUT2 | Sigma |

TABLE 1-continued

Actives tested for SGLT1 and GLUT2 inhibition activity in Caco-2 cells using 5 mM D-glucose for 15 minutes and 25 mM D-glucose for 30 minutes, respectively. The assigned class of transporter inhibited by each active is based on SGLT1 inhibitors having ≥20% inhibition of glucose transport at 5 mM D-glucose and ≤20% inhibition at 25 mM D-glucose, and GLUT2 inhibitors having ≥20% inhibition at both 5 mM and 25 mM D-glucose levels.

| Chemical Family: | Test Active[a] | Solvent | % Glucose Transport inhibition 5 mM | 25 mM | Class[b] | Supplier |
|---|---|---|---|---|---|---|
| | Luteolin-7-glucoside | DMSO | 44.09 | 17.03 | SGLT1 | Extrasynthese |
| | Apigenin-7-glucoside | DMSO | 37.97 | 12.81 | SGLT1 | Extrasynthese |
| | Apigenin-8-C-glucoside | DMSO | 33.84 | 5.76 | SGLT1 | Extrasynthese |
| Flavonols | Quercetin | DMSO | 80.78 | 61.37 | GLUT2 | Sigma |
| | Kaempferol | DMSO | 25.96 | 32.44 | GLUT2 | Sigma |
| | Myricetin | DMSO | 76.80 | 55.04 | GLUT2 | Sigma |
| | Kaempferol 7-O-glucoside | DMSO | 43.89 | 14.42 | SGLT1 | Extrasynthese |
| | Kaempferol 3-O-glucoside | DMSO | 53.89 | 19.12 | SGLT1 | Extrasynthese |
| | Quercetin-3-glucoside | DMSO | 46.40 | 12.20 | SGLT1 | PlantChem |
| | Quercetin-4-glucoside | DMSO | 43.20 | 19.05 | SGLT1 | PlantChem |
| | Quercetin-3,4'-diglucoside | DMSO | 17.48 | Nt | None | PlantChem |
| Flavanones | Naringenin | DMSO | 68.96 | 57.05 | GLUT2 | Sigma |
| | Pinocembrin | DMSO | 47.72 | 48.07 | GLUT2 | Sigma |
| | Hesperetin | DMSO | 72.34 | 74.43 | GLUT2 | Sigma |
| | Naringenin-7-O-glucoside | DMSO | 29.56 | 0.06 | SGLT1 | Extrasynthese |
| | Eriodictiol-7-O-glucoside | DMSO | 38.88 | 4.98 | SGLT1 | Extrasynthese |
| Isoflavones | Genistein | DMSO | 56.53 | 57.73 | GLUT2 | Sigma |
| | Daidze in-8-C-glucoside | DMSO | 20.31 | 12.88 | SGLT1 | Sigma |
| | Daidzein-7-glucoside | DMSO | 35.03 | 7.23 | SGLT1 | Extrasynthese |
| Anthocyanidins | Cyanidin | DMSO | 7.93 | 3.21 | None | ChromaDex |
| | Pelargonidin | DMSO | 4.07 | 16.48 | None | ChromaDex |
| | Malvidin | DMSO | 14.21 | 4.99 | None | ChromaDex |
| | Delphinindin | DMSO | 0.01 | 15.86 | None | ChromaDex |
| | Cyanidin-3-glucoside | DMSO | 42.48 | ND | SGLT1 | Extrasynthese |
| | Cyanidin-3-rutinoside | DMSO | 19.42 | ND | None | Extrasynthese |
| | Malvidin-3-O-glucoside | DMSO | 22.92 | 10.91 | SGLT1 | Extrasynthese |
| | Delphinidin-3-glucoside | DMSO | 41.27 | 13.58 | SGLT1 | Extrasynthese |
| | Pelargonidin-3-glucoside | DMSO | 27.30 | ND | SGLT1 | Extrasynthese |
| | Malvidin 3-O-Galactoside | DMSO | 19.05 | 10.41 | None | Sigma |

ND = not detected; Nt = not tested.
[a]All actives tested at 150 uM and 300 uM for GLUT2 inhibition and SGLT1 inhibition assays respectively.
[b]Based on SGLT1 inhibitors having >20% inhibition at 5 nM (glucose) and <20% inhibition at 25 mM, and GLUT2 having >20% inhibition at both 5 mM & 25 mM
ND—Not detected, Nt—Not tested Glucose Transport Cell Model Differentiated cell monolayers were washed gently in PBS (+) and the inserts transferred to a new standard tissue culture 24-well plate. The cells were incubated with fresh PBS(+) (500 µl per insert and 1 ml per well) for 30 minutes at 37° C. 5% $CO_2$. The PBS(+) was gently aspirated and replaced with 250 µl per insert of 5 mM D-glucose±test active and 1 ml of PBS(+) quickly added to each well below before the cells were replaced in the incubator at 37° C. 5% $CO_2$. After 15 minutes, the cell inserts were transferred to a new 24-well plate, and a further 250 µl of 45 mM D-glucose±test active was added to each insert (resulting in a final concentration of glucose of 25 mM) and again 1 ml of PBS(+) added to the wells. After a further 15 minutes the inserts were again transferred to a new 24-well plate and this time only fresh PBS(+) was added to the wells below. This step was repeated after another 15 minutes. The cell inserts were transferred to a new 24-well plate, the supernatant gently aspirated from the cells and replaced with 500 µl of 100 µM of Lucifer Yellow (Sigma) solution to confirm the integrity of the monolayers. 1 ml of PBS(+) was added to each well and incubated at 37° C., 5% $CO_2$ for 1 hour. The cell inserts were then discarded and the permeability of the membranes to Lucifer Yellow was checked by measuring the fluorescence of the samples at 485 nm (excitation) and 530 nm (emission) on a Spectramax Gemini EM fluorescence microplate reader.

Glucose Assay

After the last incubation, all of the retained PBS(+) from each step (i.e. at 15, 30, 45 and 60 minutes) was assayed for glucose levels as described in example 1, and the total cumulative glucose transport calculated. The localised changes in luminal glucose concentrations described and illustrated in example 1 are mimicked in-vitro through an initial short incubation of differentiated Caco-2 cells with a low level of D-glucose (5 mM for 15 minutes) immediately followed by a sustained incubation with a high level of D-glucose (final concentration of 25 mM for 45 minutes).

Figure 2:
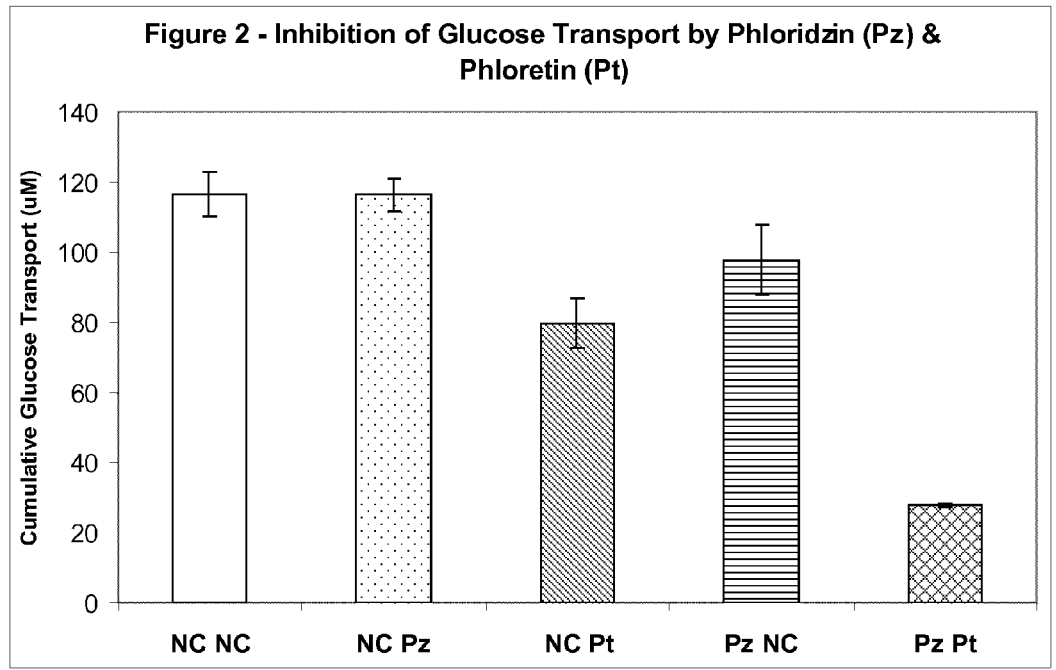
FIG. 2 the total cumulative glucose transport (μM) across differentiated Caco-2 monolayers in the presence or absence of a SGLT1 inhibitor (300 μM phloridzin (Pz)) for the first 15 minutes in 5 mM D-glucose and subsequently in the presence or absence of a GLUT2 inhibitor (125 μM phloretin (Pt)) in 25 mM D-glucose for the remaining 45 minutes (NC=vehicle negative control)

FIG. 2 plots the total cumulative glucose transport across differentiated Caco-2 monolayers in the presence or absence of a SGLT1 inhibitor for the first 15 minutes in 5 mM D-glucose and subsequently in the presence or absence of a GLUT2 inhibitor in 25 mM D-glucose for the remaining 45 minutes. To validate this cell system, phloridzin (Pz) and phloretin (Pt) were used as the widely accepted specific inhibitors of SGLT1 and GLUT2 respectively. The SGLT1 specific inhibitor, phloridzin (Pz), shows a reduction in total Cumulative Glucose Transport (tCGT) when added from the beginning of the cell system (Pz NC—horizontal striped bar), demonstrating the inhibition of SGLT1 which is the dominant active transporter at low glucose levels. However Pz exhibits no inhibition on tCGT when added later with the high concentration of D-glucose (NC Pz—dotted bar) since the SGLT1 transporters are now saturated and glucose transport is now dependent on the high capacity GLUT2 transporters. The GLUT2 specific inhibitor, phloretin (Pt), demonstrates a significant ($p \leq 0.05$) reduction in tCGT when added with the high concentration of D-glucose as expected (NC Pt—diagonal striped bars). However a combination of 300 uM Pz at low glucose concentrations, followed by 125 uM Pt at the high glucose concentration appears to significantly (p≤0.01) and synergistically inhibit the tCGT. This synergy exploits the requirement of an initial transport of glucose into the enterocyte by SGLT1 before the high-capacity GLUT2 can be targeted to the apical membrane. Used in combination, both SGLT1 and GLUT inhibitors can synergistically inhibit the localised uptake of glucose from the intestinal lumen and hence reduce the high 'spikes' of post-prandial blood glucose associated with the onset of type 2 diabetes.

Figure 3:
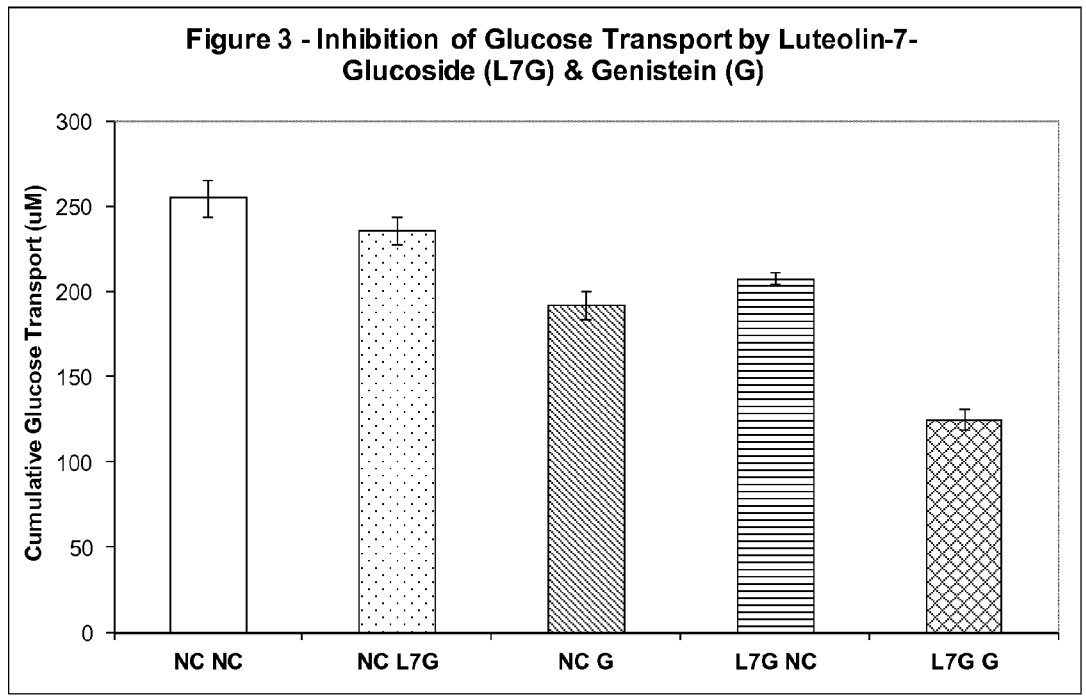
FIG. 3 the total cumulative glucose transport (μM) across differentiated Caco-2 monolayers in the presence or absence of a SGLT1 inhibitor (300 μM luteolin-7-glucoside (L7G)) for the first 15 minutes in 5 mM D-glucose and subsequently in the presence or absence of a GLUT2 inhibitor (50 μM genistein (G)) in 25 mM D-glucose for the remaining 45 minutes (NC=vehicle negative control)
Figure 4:
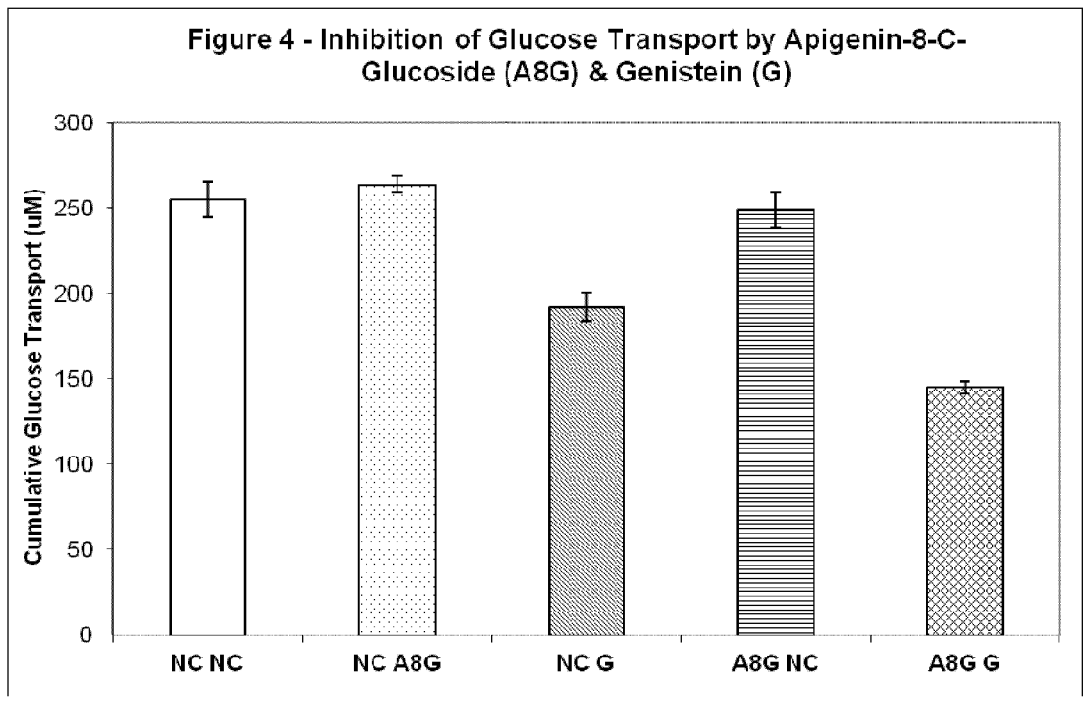
FIG. 4 the total cumulative glucose transport (μM) across differentiated Caco-2 monolayers in the presence or absence of a SGLT1 inhibitor (300 μM apigenin-8-C-glucoside (A8G)) for the first 15 minutes in 5 mM D-glucose and subsequently in the presence or absence of a GLUT2 inhibitor (50 μM genistein (G)) in 25 mM D-glucose for the remaining 45 minutes (NC=vehicle negative control)
Figure 5:
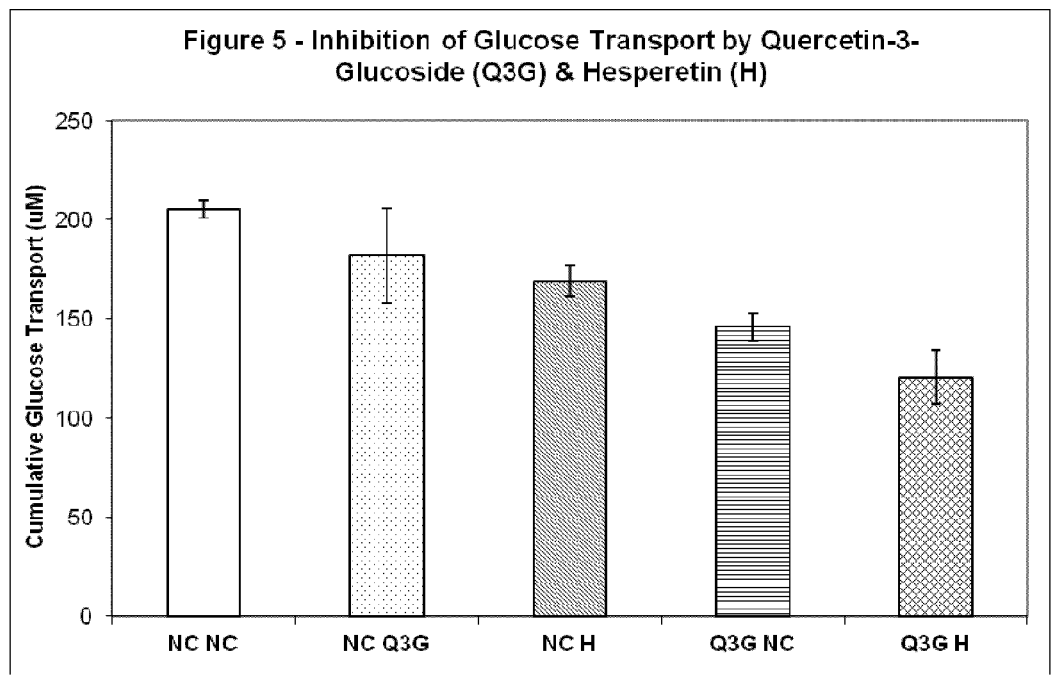
FIG. 5 the total cumulative glucose transport (μM) across differentiated Caco-2 monolayers in the presence or absence of a SGLT1 inhibitor (300 μM quercetin-3-glucoside (Q3G)) for the first 15 minutes in 5 mM D-glucose and subsequently in the presence or absence of a GLUT2 inhibitor (100 μM hesperetin (H)) in 25 mM D-glucose for the remaining 45 minutes (NC=vehicle negative control)
Figure 6:
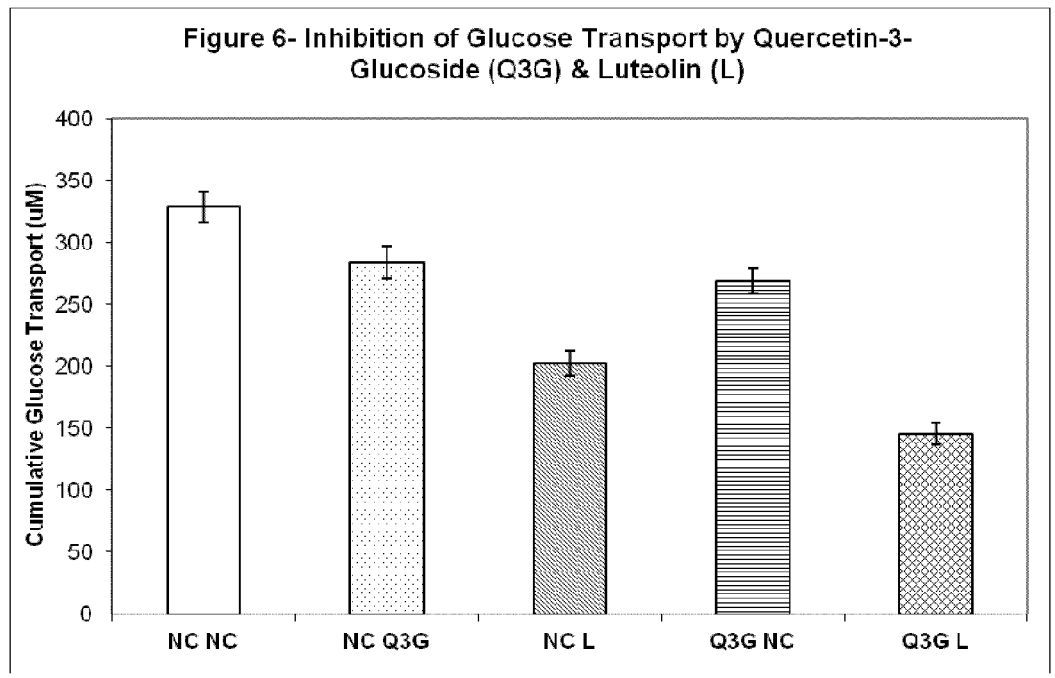
FIG. 6 the total cumulative glucose transport (μM) across differentiated Caco-2 monolayers in the presence or absence of a SGLT1 inhibitor (300 μM quercetin-3-glucoside (Q3G)) for the first 15 minutes in 5 mM D-glucose and subsequently in the presence or absence of a GLUT2 inhibitor (50 μM luteolin (L)) in 25 mM D-glucose for the remaining 45 minutes (NC=vehicle negative control)
Figure 7:
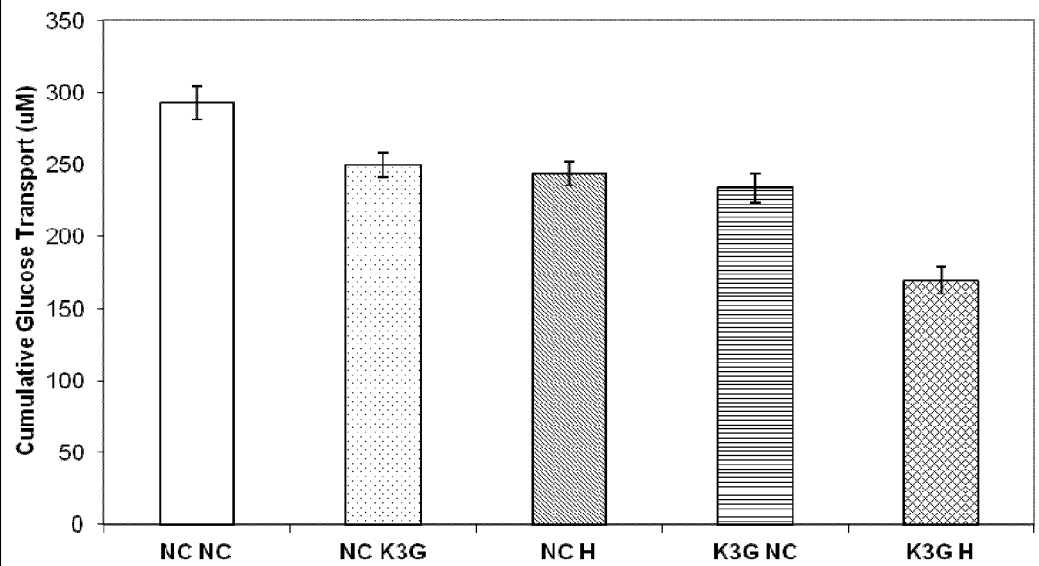
FIG. 7 the total cumulative glucose transport (μM) across differentiated Caco-2 monolayers in the presence or absence of a SGLT1 inhibitor (300 μM kaempferol-3-glucoside (K3G)) for the first 15 minutes in 5 mM D-glucose and subsequently in the presence or absence of a GLUT2 inhibitor (50 μM hesperetin (H)) in 25 mM D-glucose for the remaining 45 minutes (NC=vehicle negative control)
Figure 8:
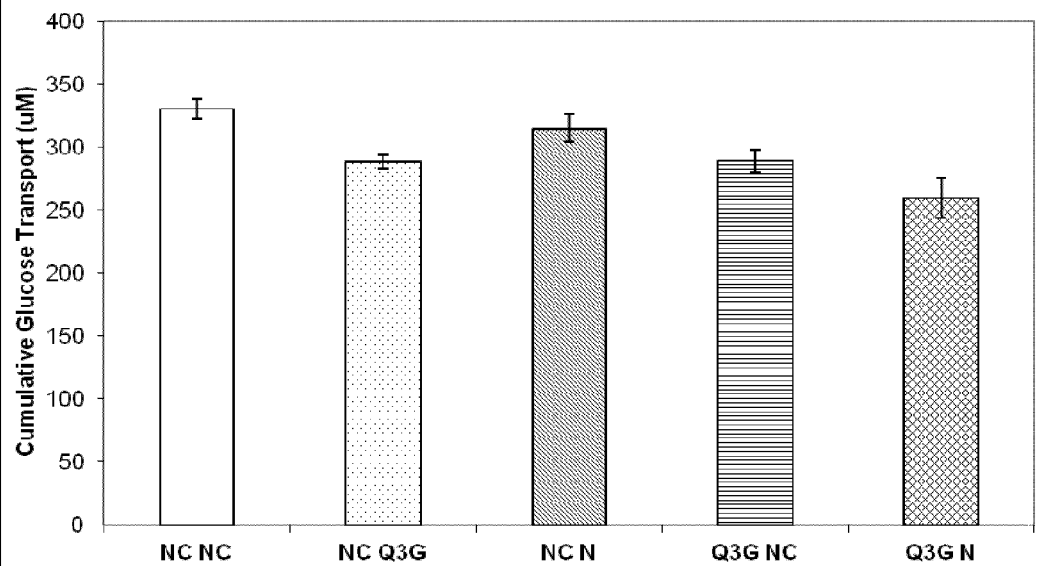
FIG. 8 the total cumulative glucose transport (μM) across differentiated Caco-2 monolayers in the presence or absence of a SGLT1 inhibitor (300 μM quercetin-3-glucoside (Q3G)) for the first 15 minutes in 5 mM D-glucose and subsequently in the presence or absence of a GLUT2 inhibitor (50 μM naringenin (N)) in 25 mM D-glucose for the remaining 45 minutes (NC=vehicle negative control)
Figure 9:
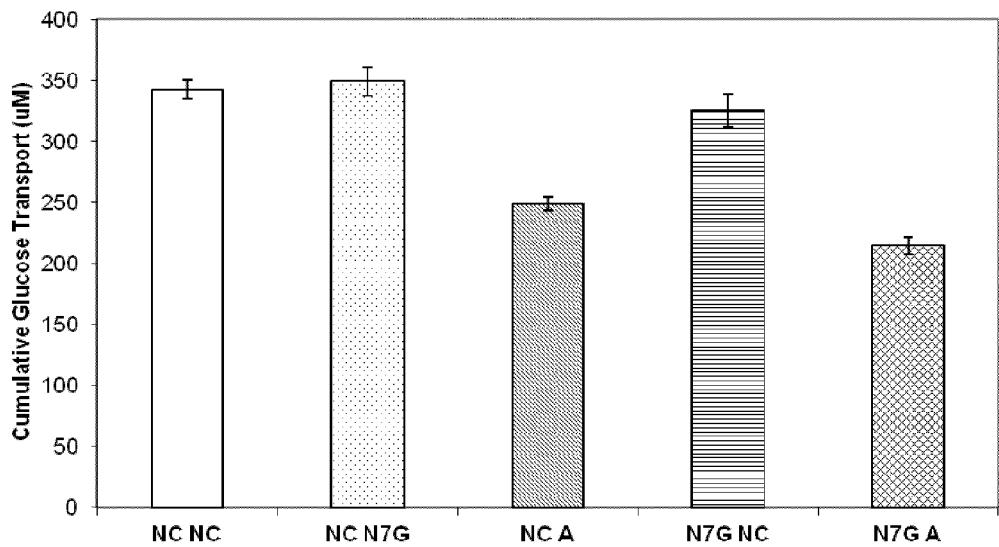
FIG. 9 the total cumulative glucose transport (μM) across differentiated Caco-2 monolayers in the presence or absence of a SGLT1 inhibitor (300 μM naringenin-7-glucoside (N7G)) for the first 15 minutes in 5 mM D-glucose and subsequently in the presence or absence of a GLUT2 inhibitor (50 μM apigenin (A)) in 25 mM D-glucose for the remaining 45 minutes (NC=vehicle negative control)
Figure 10:
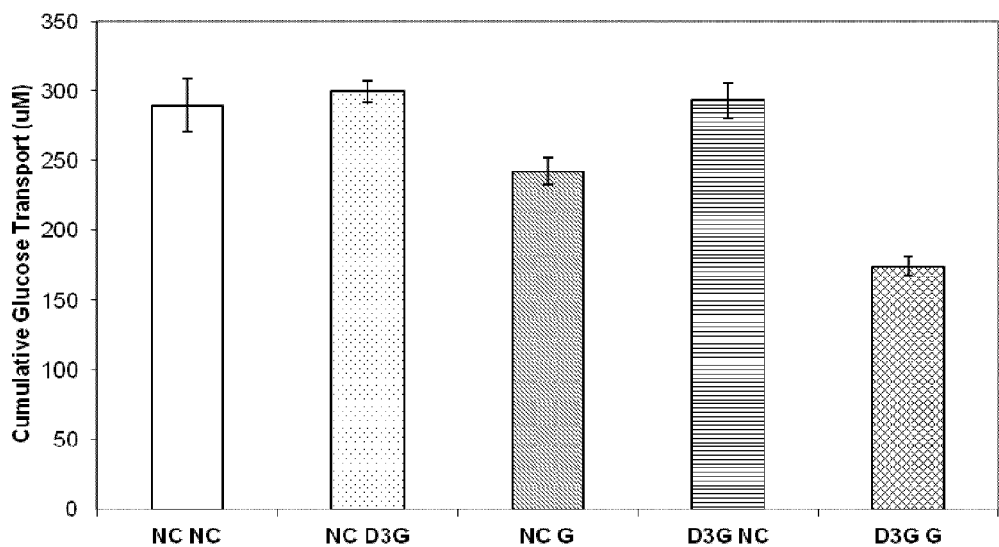
FIG. 10 the total cumulative glucose transport (μM) across differentiated Caco-2 monolayers in the presence or absence of a SGLT1 inhibitor (300 μM delphinidin-3-glucoside (D3G)) for the first 15 minutes in 5 mM D-glucose and subsequently in the presence or absence of a GLUT2 inhibitor (50 μM genistein (G)) in 25 mM D-glucose for the remaining 45 minutes (NC=vehicle negative control).

Hence any flavonoid monoglucoside identified in example 1 as specific SGLT1 inhibitors, can be combined with any flavonoid aglycone identified in example 1 as specific GLUT2 inhibitors to demonstrate the synergistic inhibition of glucose transport across a differentiated Caco-2 cell monolayer as detailed above for the combination of Pz and Pt. This is confirmed by combining the flavone monoglucosides luteolin-7-glucoside (L7G) and apigenin-8-C-glucoside (A8G) with the isoflavone aglycone genistein (FIGS. 3 and 4 respectively). Similarly, the flavonol monoglucosides quercetin-3-glucoside (Q3G) and kaempferol-3-glucoside (K3G) can be combined with the flavone aglycone luteolin and the flavanone aglycones hesperetin and naringenin to demonstrate the synergy as shown in FIGS. 5, 6, 7 and 8. Furthermore, the flavanone monoglucoside naringenin-7-glucoside (N7G) demonstrates synergistic glucose transport inhibition when combined with the flavone aglycone apigenin (FIG. 9). Finally, FIG. 10 shows the synergistic inhibition of glucose transport demonstrated by the anthocyanin delphinidin-3-glucoside (D3G) and the isoflavone aglycone genistein.

Example 3

Resistance of Flavonoid Glucosides to Human Lactase Phloridzin Hydrolase (hLPH) Degradation Preparation of Human Lactase Phloridzin Hydrolase (LPH) Extract Human epithelial colorectal adenocarcinoma (Caco-2) cells were obtained from the American Type Culture Collection (ATCC) and cultured in Dulbeco's modified eagle medium (DMEM) (with GlutaMAX™ I, 4500 mg/L D-glucose, 25 mM HEPES, Invitrogen)+10% foetal calf serum (FCS) (Sigma), MEM non essential amino acids (Fisher Scientific UK Ltd) and 1.0 mM sodium pyruvate (SIGMA) at confluence for 21 days prior to extraction with a Novagen ProteoExtract™ trans-membrane Protein Extraction kit using "Reagent A" (a mild extraction reagent for recovery of fragile protein complexes) and protease inhibitor cocktail (included in the kit). 200 µl of extract were generated from each T175 cm² flask. Extracts were stored at −80° C. in 50 ul aliquots. Prior to use extracts were semi-purified, removing low molecular weight interfering components by passing through a small G-25 Sephadex 50-100 µl spin-column (Roche or ThermoFisher Scientific).

hLPH Enzyme Assay

10 µl of semi-purified LPH extract was added to 90 µl of glucoside (1.0 mM final concentration) in 0.1 M maleate (Sigma) buffer, pH 6.0 and incubated for 60 minutes at 37° C. The reaction was terminated by addition of 200 µl 2M Tris (Sigma), pH 8.0. Concurrent blanks were run for each glucoside (1.0 mM) at 37° C. for 60 minutes adding Tris 2 M and then LPH extract only at the end. The 200 µl resultant reaction mix was passed through a small C-18 column (Sep-Pak® Light C18 cartridge 55-105 µm, Waters Ltd.) prepared with (HPLC grade methanol (VWR) and maleate buffer) x5 times to remove potential interfering hydrophobic LPH extract, substrate (glucoside) and reaction product (aglycone) components. This allowed a full recovery of glucose which was measured using the Amplex® Red Glucose/Glucose Oxidase Assay. Briefly, 100 µl of reaction reagent (0.5% 10 mM Ampliflu Red; 1.0% 10 U/ml horseradish peroxidase and 1.0% 100 U/ml glucose oxidase in phosphate buffered saline (PBS), all reagents from SIGMA) was added to 50 µl of sample and incubated at room temperature on an orbital shaker for 20 minutes. Fluorescence was read on a SpectraMax Gemini EM SN plate reader (Molecular Devices) (excitation. 530 nm and emission at 590 nm).

TABLE 2

Glucoside hydrolysis to LPH and resistance relative to Q4G. Glucosides (1.0 mM) were mixed with 10% LPH extract (Caco2 cell-line) for 1 hour at 37° C. The extent of LPH hydrolysis was assessed by measuring glucose reaction product using the Amplex ® Red Glucose/Glucose Oxidase Assay. The table lists those glucosides showing greater resistance to LPH hydrolysis than Q4G.

| Substrates (1.0 mM) | µM substrate hydrolysed/hr | Resistance to hydrolysis- % Q4G | Supplier |
| --- | --- | --- | --- |
| Q3G Quercetin-3-glucoside | 0.178 | 94.26 | SIGMA |
| K3G Kaempferol-3-glucoside | 0.224 | 92.78 | Extrasynthese |
| PLZ Phloridzin | 0.507 | 83.64 | SIGMA |
| D8G Daidzein-8-glucoside | 0.552 | 82.19 | SIGMA |
| K7G Kaempferol-7-glucoside | 0.618 | 80.05 | Extrasynthese |
| A8G Apigenin-8-glucoside | 0.685 | 77.90 | SIGMA |
| L7G Luteolin-7-glucoside | 0.814 | 73.72 | Extrasynthese |
| P3G Pelargonidin-3-glucoside | 1.272 | 58.94 | Polyphenols |
| N7G Naringenin-7-glucoside | 1.564 | 49.52 | Extrasynthese |
| Q4G Quercetin-4-glucoside | 3.098 | — | SIGMA |

Table 2 demonstrates the variation in the degradation rates of different flavonoid glucosides by hLPH. Whilst Q4G demonstrates the highest degree of degradation by hLPH, Q3G appears to be approximately 95% more resistant to hLPH in this assay than Q4G. Similarly, the other eight glucosides all exhibit increased resistance to hLPH relative to Q4G, ranging from 49.5% for N7G to 92.8% for K3G. Consequently, these glucosides would be less liable to hydrolysis by hLPH in the intestine during a meal and thus potentially prolonging its activity as a SGLT1 inhibitor. Therefore selecting flavonoid glucosides with at least a 20% increased resistance to hLPH than Q4G would be beneficial in prolonging any glucoside-specific activity in vivo.

Example 4

Bottled Water

A dry powder comprising 200 mg quercetin-3-glucoside per gram and 125 mg luteolin per gram and also comprising flavours is added to water at a level of 2 grams of dry powder per liter of water. The formulation is dispensed into 250 mls bottles and sealed. Each bottle is labelled "1-a-day" or words to that effect. Each bottle therefore delivers a daily dose of 100 mgs quercetin-3-glucoside and 62.5 mgs of luteolin.

Example 5

Sachets for Adding to a Meal

A dry powder comprising 100 mg of luteolin-7-glucoside per gram and 60 mg of genistein per gram and also comprising flavours is dispensed into sachets at the level of 1 gram per sachet and sealed. Each sachet is labelled "1-a-day" or words to that effect.

The invention claimed is:

1. An edible composition comprising:
   5 to 10% dry weight genistein; and
   5 to 10% dry weight of at least one flavonoid monoglucoside selected from the group consisting of luteolin-7-glucoside, apigenin-8-C-glucoside, kaempferol-7-O-glucoside, kaempferol-3-O-glucoside, naringenoin-7-O-glucoside, daidzein-8-glucoside, cyanidin-3-glucoside, quercetin-3-glucoside, pelagonidin-3-glucoside, malvidin-3-glucoside, delphinidin-3-glucoside and mixtures thereof,
   wherein the flavonoid monoglucoside is at least 20%, more resistant to hydrolysis by lactase phloridzin hydrolase than quercetin-4-glucoside, and
   wherein the flavonoid aglycone is a GLUT 2 inhibitor and the flavonoid monoglucoside is a SGLT 1 inhibitor, and
   wherein the edible composition is pre-packaged.

2. A method of reducing post-prandial blood glucose peak amplitude or glycemic response in a non-diabetic person comprising the steps of:
   (a) oral administration of the composition of claim 1 to the non-diabetic person; and
   (b) oral administration of saccharide to the non-diabetic person;
   wherein step (a) is simultaneous with, precedes by 0 to 90 minutes, or follows by 0 to 30 minutes step (b), and
   wherein the saccharide comprises glucose.

3. A method for treating a person in need thereof for type 2 diabetes, the method comprising the steps of:
   (a) oral administration of the composition of claim 1 to the person in need thereof; and
   (b) oral administration of saccharide to the person in need thereof;
   wherein step (a) is simultaneous with, precedes by 0 to 90 minutes, or follows by 0 to 30 minutes step (b), and
   wherein the saccharide comprises glucose.

4. A method according to claim 2 wherein the saccharide is selected from the group consisting of polysaccharide, oligosaccharide, disaccharide, monosaccharide and mixtures thereof.

5. Composition according to claim 1 for use in reducing post-prandial blood glucose peak amplitude or glycemic response in a non-diabetic person.

6. Composition according to claim 1 for use in the treatment of type 2 diabetes.

7. The composition of claim 1, further comprising flavors.

* * * * *